(12) United States Patent
Kim et al.

(10) Patent No.: US 9,880,270 B2
(45) Date of Patent: Jan. 30, 2018

(54) TEST DEVICE AND IMAGING DEVICE INCLUDING THE SAME

(71) Applicant: Samsung Electronics Co., Ltd., Suwon-si, Gyeonggi-do (KR)

(72) Inventors: Jae-hong Kim, Seoul (KR); Yoshihiko Hayashi, Seongnam-si (KR); Akinori Okubo, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 259 days.

(21) Appl. No.: 14/883,753

(22) Filed: Oct. 15, 2015

(65) Prior Publication Data

US 2016/0116578 A1 Apr. 28, 2016

(30) Foreign Application Priority Data

Oct. 27, 2014 (KR) .................. 10-2014-0146433

(51) Int. Cl.
| | | |
|---|---|---|
| G01S 7/52 | (2006.01) | |
| G01S 15/89 | (2006.01) | |
| G10K 11/34 | (2006.01) | |
| G01N 29/06 | (2006.01) | |
| G01N 29/26 | (2006.01) | |
| G01S 17/89 | (2006.01) | |
| G01S 13/89 | (2006.01) | |

(52) U.S. Cl.
CPC ........ *G01S 7/5205* (2013.01); *G01N 29/0654* (2013.01); *G01N 29/262* (2013.01); *G01S 7/52025* (2013.01); *G01S 7/52047* (2013.01); *G01S 7/52077* (2013.01); *G01S 15/8915* (2013.01); *G01S 15/8925* (2013.01); *G01S 15/8929* (2013.01); *G10K 11/346* (2013.01); *G01N 2291/044* (2013.01); *G01S 13/89* (2013.01); *G01S 17/89* (2013.01)

(58) Field of Classification Search
CPC . G01S 7/5205; G01S 7/52047; G01S 7/52077
See application file for complete search history.

(56) References Cited

U.S. PATENT DOCUMENTS

| | | |
|---|---|---|
| 4,487,069 A | 12/1984 | Ishikawa et al. |
| 4,541,281 A | 9/1985 | Chubachi et al. |
| 4,563,898 A | 1/1986 | Kanda et al. |
| 4,893,510 A | 1/1990 | Ichikawa et al. |
| 5,079,952 A | 1/1992 | Nakaso et al. |
| 5,553,499 A | 9/1996 | Hisata et al. |
| 6,301,967 B1 | 10/2001 | Donskoy et al. |
| 6,389,885 B1 | 5/2002 | Arnold et al. |

(Continued)

FOREIGN PATENT DOCUMENTS

KR  10-1996-0009763  7/1996

*Primary Examiner* — Hovhannes Baghdasaryan
(74) *Attorney, Agent, or Firm* — Myers Bigel, P.A.

(57) ABSTRACT

A test device includes a plurality of transceivers that respectively transmit a wave to a test target point of a test object, respectively receive a wave reflected, scattered, or refracted from the test object, and respectively output a signal generated in response to the received wave; a combiner that combines the plurality of received signals generated by the plurality of transceivers; and a plurality of switches that are opened or closed to transfer the plurality of received signals to the combiner or block the plurality of received signals from being transferred to the combiner.

13 Claims, 9 Drawing Sheets

(56) References Cited

U.S. PATENT DOCUMENTS

| | | | |
|---|---|---|---|
| 6,795,009 B2 * | 9/2004 | Duffy | H02M 3/157 323/283 |
| 6,821,251 B2 | 11/2004 | Alexandru | |
| 7,600,442 B2 | 10/2009 | Hirose et al. | |
| 2002/0165453 A1 * | 11/2002 | Bae | G01S 7/52023 600/437 |
| 2007/0122155 A1 * | 5/2007 | Hillis | H01Q 3/2676 398/115 |
| 2009/0105592 A1 * | 4/2009 | Yao | A61B 8/0883 600/447 |

* cited by examiner

TEST DEVICE AND IMAGING DEVICE INCLUDING THE SAME

CROSS-REFERENCE TO RELATED APPLICATION

This application claims priority to Korean Patent Application No. 10-2014-0146433, filed on Oct. 27, 2014, the disclosure of which is incorporated herein in its entirety by reference.

FIELD OF THE INVENTION

The inventive concept relates to a test device including a plurality of transceivers and an imaging device including the test device.

BACKGROUND

A test device may include a transceiver that transmits a wave to a test object and receives a wave reflected, scattered, or refracted from the test object. The transmitted wave and the received wave may be used for acquiring information on the test object.

Generally, the test device may detect information on a test target point while the test target point and a transceiver are in 1:1 correspondence. However, the test target point is inside the test object, noise may be generated by other components of the test object, and thus, the reception sensitivity may be low.

SUMMARY

The inventive concept provides a test device that exhibits high reception sensitivity with respect to test target points of a test object and an imaging device including the same.

According to an aspect of the inventive concept, there is provided a test device including: a plurality of transceivers configured to respectively transmit a wave to a test target point of a test object, to respectively receive a wave reflected, scattered, and/or refracted from the test object, and to respectively generate and output a signal in response to the received wave; a combiner configured to combine the signals generated by the plurality of transceivers; and a plurality of switches configured to selectively transfer the signals to the combiner and to selectively block the received signals from being transferred to the combiner.

In some embodiments, the waves transmitted by the plurality of transceivers may be focused on the test target point.

In some embodiments, the wave received by any one of the plurality of transceivers may include waves reflected, scattered, and/or reflected in response to the waves transmitted by the other transceivers.

In some embodiments, the test device may further include a switch control unit configured to control opening and closing of the plurality of switches to selectively transfer the signals to the combiner and to selectively block the received signals from being transferred to the combiner.

In some embodiments, the switch control unit may close the switch corresponding to at least one of the generated signals having a reduced level of noise from among the generated signals and open the switches corresponding to the other generated signals.

In some embodiments, the test object may include a semiconductor structure having an irregular wiring density, and the switch control unit may control the plurality of switches such that at least one of the generated signals corresponding to the reflected, scattered, or refracted wave passing through a region with a lowest wiring density is transferred to the combiner and the other generated signals are blocked.

In some embodiments, the plurality of switches may be further configured so that opening and closing thereof are reset according to a change of the test target point.

In some embodiments, an input angle of the wave transmitted from any one of the plurality of transceivers to the test target point may be different from a reflection angle of the wave received by the transceiver, which corresponds to the received signal transferred to the combiner.

In some embodiments, the plurality of transceivers may be arranged in a matrix form.

In some embodiments, the plurality of transceivers may be arranged in a multilayer structure.

In some embodiments, the plurality of transceivers may be arranged in a spherical shape.

In some embodiments, the wave may be a sound wave, and each of the transceivers may include a piezoelectric element that receives the reflected, scattered, or refracted wave from the test object and converts the received wave into an electric signal.

In some embodiments, the wave may be an electromagnetic wave, and each of the transceivers may include a photoelectric element that receives the reflected, scattered, or refracted wave from the test object and converts the received wave into an electric signal.

In some embodiments, the electromagnetic wave may be a terahertz wave, an X-ray, an infrared ray, or a micro wave.

In some embodiments, the test device may further include a display unit configured to display an image of the test object in response to the generated signals transferred to the combiner.

According to an aspect of the inventive concept, there is provided an ultrasonic imaging device including: a plurality of ultrasonic transceivers, each of the plurality of ultrasonic transceivers including a piezoelectric element that is configured to transmit an ultrasonic wave to a test object and is configured to receive an echo ultrasonic wave generated from the test object and generate and output a signal in response to the received echo ultrasonic wave; a combiner that combines the signals generated by the plurality of ultrasonic transceivers; and a plurality of switches between the plurality of ultrasonic transceivers and the combiner, the plurality of switches being configured to open or close to selectively transfer the generated signals to the combiner or to selectively block the generated signals from being transferred to the combiner, wherein the plurality of switches are further configured to close and selectively block at least one of the generated signals that contains a relatively high level of noise from among the generated signals and the opening and closing of the plurality of switches are reset according to a change in a position of the test object.

According to an aspect of the inventive concept, there is provided a test device including: a plurality of transceivers configured to respectively transmit a wave to a test target point of a test object, to respectively receive a wave reflected, scattered, and/or refracted from the test object, and to respectively generate and output a signal in response to the received wave; a controller configured to select ones of the signals generated by the plurality of transceivers having relatively low levels of noise; and a combination unit configured to receive the selected ones of the signals generated by the plurality of transceivers having relatively low levels of noise and to output a combined signal.

In some embodiments, the test device further comprises a plurality of switches configured to selectively transfer the signals to the combiner and to selectively block the received signals from being transferred to the combiner, and the controller comprises a switch control unit configured to control the plurality of switches to selectively transfer the selected ones of the signals generated by the plurality of transceivers having relatively low levels of noise.

In some embodiments, the waves transmitted by the plurality of transceivers are focused on the test target point.

In some embodiments, the plurality of switches are further configured so that opening and closing thereof are reset according to a change of the test target point.

In some embodiments, an input angle of the wave transmitted from any one of the plurality of transceivers to the test target point is different from a reflection angle of the wave received by the transceiver, which corresponds to the received signal transferred to the combiner.

According to an aspect of the inventive concept, there is provided a test device including: a first transceiver and a second transceiver configured to respectively transmit an input wave to a test object and respectively receive a reflected wave; a combiner that receives a first signal and a second signal respectively output by the first transceiver and the second transceiver in response to the received reflected waves; and a first switch between the first transceiver and the combiner, and a second switch between the second transceiver and the combiner.

In some embodiments, the reflected wave may include a first input wave transmitted from a transmitter of the first transceiver and a second input wave transmitted from a transmitter of the second transceiver.

In some embodiments, the first switch and the second switch may be configured such that either of the first switch and the second switch is opened so that one from the first signal and the second signal that contains more noise is blocked from being transmitted to the combiner.

In some embodiments, the input wave may be a sound wave or an electromagnetic wave.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF THE EMBODIMENTS

Hereinafter, embodiments of the inventive concept will be described with reference to the accompanying drawings.

The inventive concept may, however, be embodied in many different forms and should not be construed as being limited to the embodiments set forth herein; rather, these embodiments are provided so that this disclosure will be thorough and complete, and will fully convey the inventive concept to those of ordinary skill in the art. It should be understood, however, that there is no intent to limit the inventive concept to the particular forms disclosed, but on the contrary, the inventive concept is to cover all modifications, equivalents, and alternatives falling within the spirit and scope of the inventive concept. Like reference numerals denote like elements throughout the specification and drawings. In the drawings, the dimensions of structures are exaggerated or reduced for clarity of the inventive concept.

Also, though terms "first" and "second" are used to describe various members, components, regions, layers, and/or portions in various embodiments of the inventive concept, the members, components, regions, layers, and/or portions are not limited to these terms. These terms are used only to differentiate one member, component, region, layer, or portion from another one. Therefore, a member, a component, a region, a layer, or a portion referred to as a first member, a first component, a first region, a first layer, or a first portion in an embodiment may be referred to as a second member, a second component, a second region, a second layer, or a second portion in another embodiment.

Unless otherwise defined, all terms used herein, including technical and scientific terms, have the same meaning as commonly understood by one of ordinary skill in the art to which the inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

When a certain embodiment may be implemented differently, a specific process order may be performed differently from the described order. For example, two consecutively described processes may be performed substantially at the same time or performed in an order opposite to the described order.

In the accompanying drawings, the modifications of the illustrated shapes may be expected according to manufacturing technologies and/or tolerance. Therefore, the exemplary embodiments should not be construed as being limited to specific shapes of the illustrated regions. The shapes may be changed during the manufacturing processes.

Figure 1:
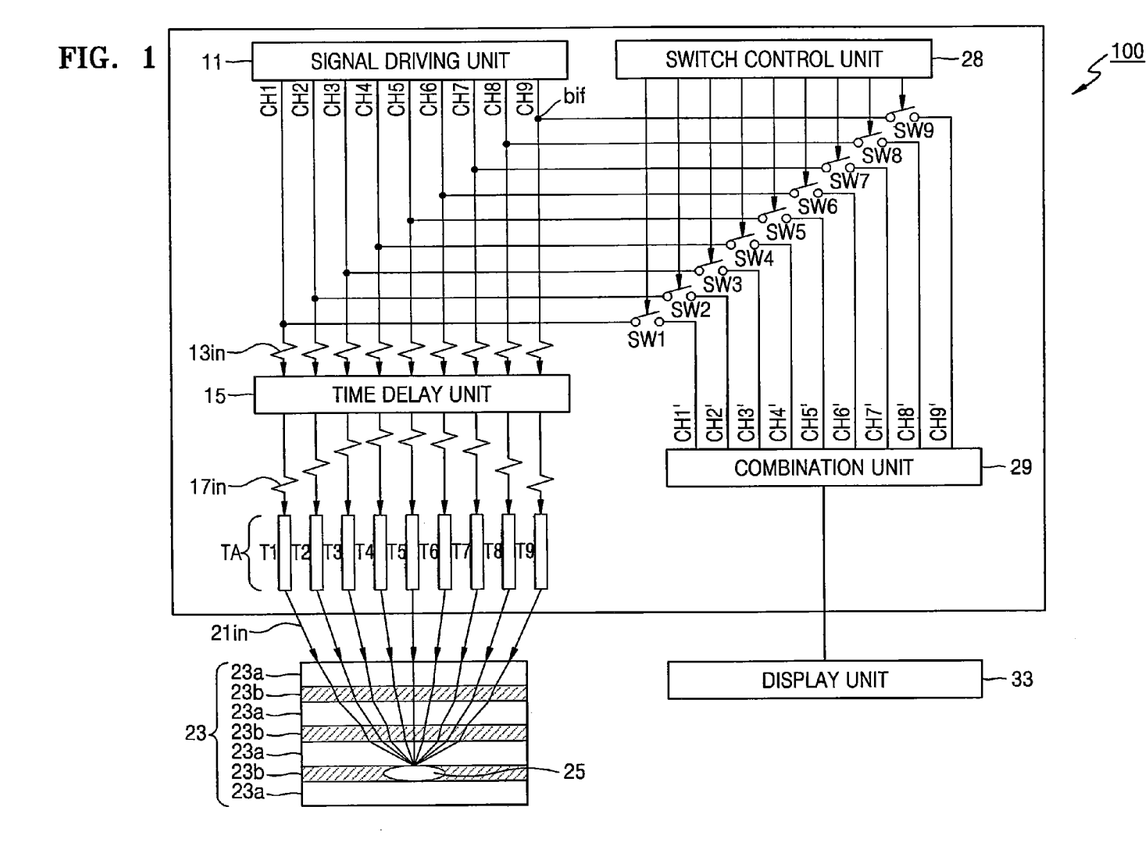
FIG. 1 is a diagram illustrating a signal transmission of a test device, according to an exemplary embodiment of the inventive concept.
Figure 2:
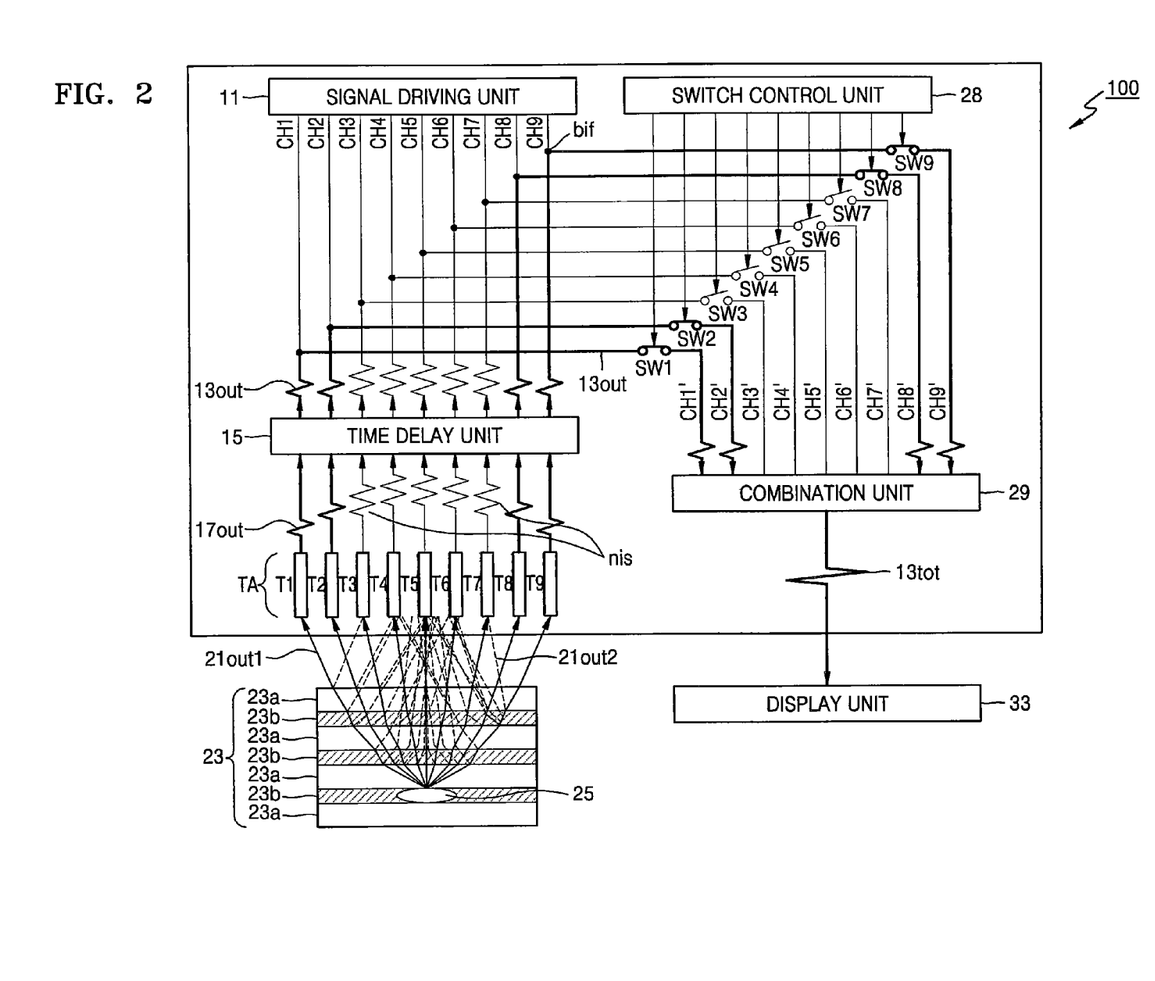
FIG. 2 is a diagram illustrating a signal reception of the test device of FIG. 1, according to an exemplary embodiment of the inventive concept.

FIG. 1 is a diagram illustrating a signal transmission of a test device 100, according to an exemplary embodiment of the inventive concept, and FIG. 2 is a diagram illustrating a signal reception of the test device 100 of FIG. 1, according to an exemplary embodiment of the inventive concept.

Referring to FIGS. 1 and 2, the test device 100 may include a signal driving unit 11 that generates pulse signals 13in, a time delay unit 15 that adjusts timings of the pulse signals 13in, a plurality of transceivers T1 to T9 that receive a timing-adjusted pulse signal 17in, transceive waves 21in, 21out1, and 21out2 to/from a test object 23, and output a plurality of received signals 17out, a combination unit 29 that combines a plurality of timing-adjusted received signals 13out, and a plurality of switches SW1 to SW9 that select some of the timing-adjusted received signals 13out transferred from the combination unit 29. The combination unit 29 may include at least one combiner.

The test device 100 may output a combined received signal 13tot by combining the received signals selected by the switches SW1 to SW9. The switches SW1 to SW9 may be closed such that the received signals 13out containing small noise signals nis among the received signals 13out are transferred to the combination unit 29, and the switches SW1 to SW9 may be opened such that the received signals 13out containing many noise signals nis are not transferred to the combination unit 29. Accordingly, since the received signals 13out transferred to the combination unit 29 contain small noise signals nis, the test device 100 may acquire the high-quality combined received signal 13tot.

The test device 100 may further include a switch control unit 28 that controls the opening and closing of the switches SW1 to SW9. The switch control unit 28 may be set to open and close the switches SW1 to SW9 according to the magnitudes of the noise signals nis contained in the received signals 13out.

The test device 100 is illustrated as including nine transceivers T1 to T9, but the exemplary embodiment is not limited thereto. According to the exemplary embodiment, any suitable number of the transceivers T1 to T9 may be used, as long as the test device 100 includes a plurality of transceivers. Accordingly, the test device 100 may include two to eight transceivers or may include ten or more transceivers.

In addition, the nine transceivers T1 to T9 included in the test device 100 are illustrated as being arranged in a row, but the exemplary embodiment is not limited thereto. According to the exemplary embodiment, the plurality of transceivers included in the test device 100 may be arbitrarily arranged. The arrangement of the plurality of transceivers will be described below with reference to FIGS. 7 to 9.

In some exemplary embodiments, the test device 100 may be included in an imaging device. That is, an image of the test object 23 may be implemented by transferring the combined received signal 13tot from the combination unit 29 to a display unit 33. As described above, since it is possible to acquire the high-quality combined received signal 13tot by the selection of the switches SW1 to SW9, the imaging device including the test device 100 may provide an accurate image of the test object 23.

The signal transmission of the test device 100 will be described below in detail with reference to FIG. 1. Since the test device 100 as illustrated includes the nine transceivers T1 to T9, the signal driving unit 11, the time delay unit 15, the switch control unit 28, and the combination unit 29 are connected to one another through nine channels CH1 to CH9.

The signal driving unit 11 may generate the pulse signals 13in and transfer the generated pulse signals 13in to the time delay unit 15. At this time, the nine pulse signals 13in in generated through the nine channels CH1 to CH9 may be transferred to the time delay unit 15 through the nine channels CH1 to CH9, respectively.

The nine pulse signals 13in may be transferred to the time delay unit 15 at the same timing. The time delay unit 15 may adjust the timings of the nine pulse signals 13in transferred at the same timing. According to the exemplary embodiment, the plurality of transceivers T1 to T9 may be used for testing one test target point 25 of the test object 23. That is, the plurality of transceivers T1 to T9 may generate a plurality of input waves 21in focused on one test target point 25, and the plurality of transceivers T1 to T9 may be driven for detecting reflected waves 21out1 and 21out2. Therefore, the timings of the nine pulse signals 13in may be adjusted such that the nine waves 21in generated by the nine pulse signals 17in are focused on the test object 23. That is, the nine waves 21in may be focused on the test target point 25 by adjusting the transmission timings of the nine pulse signals 13in.

Specifically, the timings of the nine pulse signals 17in having undergone a time delay in the time delay unit 15 may be adjusted like waveforms appearing on the nine channels CH1 to CH9. That is, the timings of the nine pulse signals 17in may be adjusted such that the pulse signal 17in passing through the fifth transceiver T5 closest to the test target point 25 has a large time delay, and the pulse signals 17in passing through the first and ninth transceivers T1 and T9 farthest from the test target point 25 have a small time delay. Similarly, the timings of the nine pulse signals 17in may be adjusted such that the second to eighth transceivers T2 to T8 have time delays according to the distance from the test target point 25.

The nine timing-adjusted pulse signals 17in may be transferred to the nine transceivers T1 to T9, respectively. Accordingly, the nine transceivers T1 to T9 may generate nine input waves 21in, respectively.

The nine input waves 21in may form a wave field in the test object 23 and be transmitted such that the waves are focused on the test target point 25.

In FIG. 1, the test object 23 may be a semiconductor device in which insulating layers 23a and metal wiring layers 23b are alternately stacked. Since the insulating layers 23a and the metal wiring layers 23b are stacked, the respective layers are provided with different materials. Thus, each of the nine input waves 21in may be refracted in the respective layers.

Next, the signal reception of the test device 100 will be described below in detail with reference to FIG. 2. Since the same reference numerals denote the same elements, a redundant description thereof will be omitted. The nine input waves 21in of FIG. 1 are incident with focusing on the test target point 25 of the test object 23, and the plurality of reflected waves 21out1 are generated. At this time, the reflected waves 21out1 may be scattered or refracted by other adjacent materials. Thus, as compared with the input waves 21in of FIG. 1, the amplitudes of the reflected waves 21out1 may be reduced or the phases thereof may be changed, resulting in an occurrence of noise. In particular, the test object 23 has the stack structure of the insulating layers 23a and the metal wiring layers 23b, which may disturb the reflected waves 21out2 from the surfaces of the insulating layers 23a and the metal wiring layers 23b. The disturbed reflected waves 21out2 may serve as main noise that may rapidly reduce the reception sensitivities of the reflected waves 21out1 generated from the test target point 25.

The nine transceivers T1 to T9 receive the reflected waves 21out1. At this time, the reflected wave 21out1 received by the first transceiver T1 does not contain only the reflected wave generated by the input wave 21in that is generated by the first transceiver T1. That is, the reflected wave 21out1 received by the first transceiver T1 may contain the reflected waves 21out1 generated by the input waves 21in that are generated by the second to ninth transceivers T2 to T9. Similarly, the reflected wave 21out1 received by any one of the second to ninth transceivers T2 to T9 may contain the reflected waves generated by the input waves that are generated by the other transceivers.

The disturbed reflected waves 21out2 may be transmitted to some of the nine transceivers T1 to T9 more than others. In FIG. 2, the disturbed reflected waves 21out2 are transmitted more to the third to seventh transceivers T3 to T7.

The nine transceivers T1 to T9, which receive the reflected waves 21out1 and the disturbed reflected waves 21out2, may generate nine received signals 17out, respectively. The nine received signals 17out appear as waves on the nine channels CH1 to CH9. The received signals 17out, which pass through the third to seventh channels CH3 to CH7 connected to the third to seventh transceivers T3 to T7 receive relatively more disturbed reflected waves 21out2, which may contain relatively more noise signals nis.

The nine received signals 17out may be transferred to the time delay unit 15. As described above, since the distances between the test target point 25 and the nine transceivers T1 to T9 are different, the timings of the nine received signals 17out are different. The time delay unit 15 may adjust the timings of the nine received signals 17out. In this case, the time delay provided to the channels CH1 to CH9 by the time delay unit 15 may be reversely applied. The time delay unit 15 may perform adjustment such that the timings of the received signals 13out passing through the nine channels CH1 to CH9 become substantially equal to one another. However, even in these cases, the noise signals nis generated by the disturbed reflected waves 21out2 are not derived from the test target point 25, and the timing cannot be adjusted by the time delay unit 15. Therefore, the timings of the received signals 13out passing through the third to seventh channels CH3 to CH7 containing relatively more noise signals nis derived from the disturbed reflected waves 21out2 may be different from the timings of the received signals 13out passing through the first, second, eighth, and ninth channels CH1, CH2, CH8, and CH9, which contain relatively fewer noise signals nis.

The nine received signals 13out having undergone the time delay unit 15 may be transferred to the combination unit 29 through first to ninth channels CH1' to CH9' that transfer the nine received signals 13out. The first to ninth channels CH1' to CH9' may be branched from nodes bif of the nine channels CH1 to CH9 that connect the signal driving unit 11 and the time delay unit 15.

In order to select the received signals 13out to be transferred to the combination unit 29, first to ninth switches SW1 to SW9 may be provided at the first to ninth channels CH1' to CH9'. Since the received signals 13out passing through the third to seventh channels CH3' to CH7' contain relatively greater noise signals nis, the third to seventh switches SW3 to SW7 may be opened to block the received signals 13out containing the noise signals nis from being transferred to the combination unit 29. The first, second, eighth, and ninth switches SW1, SW2, SW8, and SW9 maintain the closed state, and the received signals 13out passing through the first, second, eighth, and ninth channels CH1', CH2', CH8', and CH9' are transferred to the combination unit 29. In this manner, the combined received signal 13tot may be generated. The combined received signal 13tot, to which a reduced amount or no noise signals are transferred, may more accurately reflect information on the test target point 25.

In order to control the opening and closing of the first to ninth switches SW1 to SW9, the test device 100 may further include a switch control unit 28 connected to the first to ninth switches SW1 to SW9. The switch control unit 28 may open the switches SW1 to SW9 when the magnitudes of the noise signals nis contained in the received signals 13out are out of a predetermined range. However, in order to control the opening and closing of the first to ninth switches SW1 to SW9, a tester may select the opening and closing of the first to ninth switches SW1 to SW9, without including the switch control unit 28.

As described above, in the test device 100, the plurality of transceivers T1 to T9 may be disposed near the test object 23, generate the plurality of input waves 21in focused on one test target point 25, and detect the reflected waves 21out1 and 21out2. Since the plurality of received signals 17out are obtained with respect to one test target point 25 through the plurality of transceivers T1 to T9, it is possible to select the received signals 17out that reflect a relatively more accurate test result.

In addition, among the received signals 13out obtained from the plurality of transceivers T1 to T9, the received signals 13out containing relatively higher levels of noise signals nis may be removed through the plurality of switches SW1 to SW9, and thus, only the received signals 13out reflecting a more accurate test result are extracted. Accordingly, it is possible to realize the test device 100 having high reception sensitivity.

Furthermore, since the test device 100 includes the plurality of transceivers T1 to T9, all points of the test object 23 may be within a predetermined distance suitable to transceive the input waves 21in and the reflected waves 21out1. Therefore, even when the test target point 25 is changed within the test object 23, all points of the test object 23 may be tested without moving the test device 100 on the test object 23. The test device 100 according to the exemplary embodiment may transceive signals having high reception sensitivity in a short time.

The test device 100 according to the exemplary embodiment may solve the limitation occurring when one transceiver is installed. That is, in a case where one transceiver is included in the test device, one test target point is tested by one transceiver. Thus, as described above, the noise signals generated by the multilayer structure are inevitably contained in the received signals, resulting in the reduction in the reception sensitivity. In addition, a long time may be taken to test all points of the test object because one transceiver needs to pass through all points of the test object.

Furthermore, the test device 100, in which the plurality of transceivers T1 to T9 are used for testing one test target point 25, may solve the limitation occurring in the test device that simply includes a plurality of transceivers. That is, the test device that simply includes the plurality of transceivers needs to be mechanically moved so as to test all points of the test object. However, in a case where only the plurality of transceivers are simply included, the plurality of transceivers are not used for testing one test target point, but are respectively used for testing all points therebelow. Since one transceiver is driven for one test target point, it is possible to reduce or avoid the problem that the noise signals are contained in the received signals.

In some exemplary embodiments, the test device 100 may be a test device that detects a defect of the test object 23. The defect of the test object 23 may be detected from different aspects of response to the waves as compared to adjacent materials. The defect may be a void or a crack.

In some embodiments, the test device 100 may be included in an imaging device. The combined received signal 13tot, which is obtained with respect to the test target point 25 by using the test device 100, may be transferred to the display unit 33 to implement a two-dimensional or three-dimensional image of the test target point 25. Since the imaging device using the test device 100 reduces the influence of the noise signals, it is possible to implement a high-quality test image.

Figure 3:
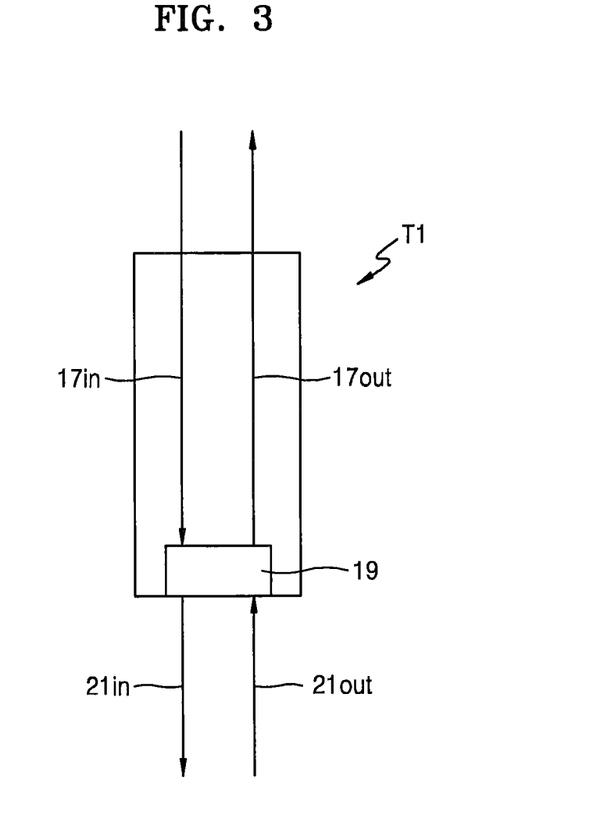
FIG. 3 is a schematic diagram of a transceiver included in the test device of FIGS. 1 and 2, according to an exemplary embodiment.

FIG. 3 is a schematic diagram of the transceiver T1 according to an exemplary embodiment.

Referring to FIG. 3, the transceiver T1 included in the test device 100 of FIGS. 1 and 2 may include a conversion element 19 that converts the electrical pulse signal 17in transferred from the time delay unit 15 into the input wave 21in. The conversion element 19 may electrically convert the reflected wave 21out into the received signal 17out.

In some embodiments, a transmitter included in the transceiver T1 may generate a sound wave. That is, the input wave 21in and the reflected wave 21out may be sound waves. For example, the sound wave may be an ultrasonic wave, a high-frequency wave, or a low-frequency wave. Accordingly, the conversion element 19 may be a piezoelectric element that converts an electric signal into a mechanical pressure, and vice versa.

In some embodiments, a transmitter included in the transceiver T1 may generate an electromagnetic wave. That is, the input wave 21in and the reflected wave 21out may be electromagnetic waves. For example, the input wave 21in and the reflected wave 21out may be a terahertz wave, an X-ray, an infrared ray, or a micro wave. Accordingly, the conversion element 19 may be a photoelectric element that converts an electromagnetic wave into an electric signal.

In some embodiments, the plurality of transceivers T1 to T9 included in the test device 100 may test the test object 23 by transceiving an ultrasonic wave. In this case, conversion elements 19 included in the plurality of transceivers T1 to T9 may be piezoelectric elements. Accordingly, the test device 100 may be included in an inspection apparatus using an ultrasonic wave. The inspection apparatus using the ultrasonic wave may be used for detecting a defect of a semiconductor device or a semiconductor package. With the increase in the integration degree of semiconductor devices, a design rule for elements of the semiconductor devices has been reduced or made smaller. Thus, a semiconductor device manufacturing process is becoming more difficult. Even when a fine void or crack occurs in the semiconductor device, the operation of the semiconductor device may be greatly degraded. Hence, it is necessary to test such a defect.

Figure 4:
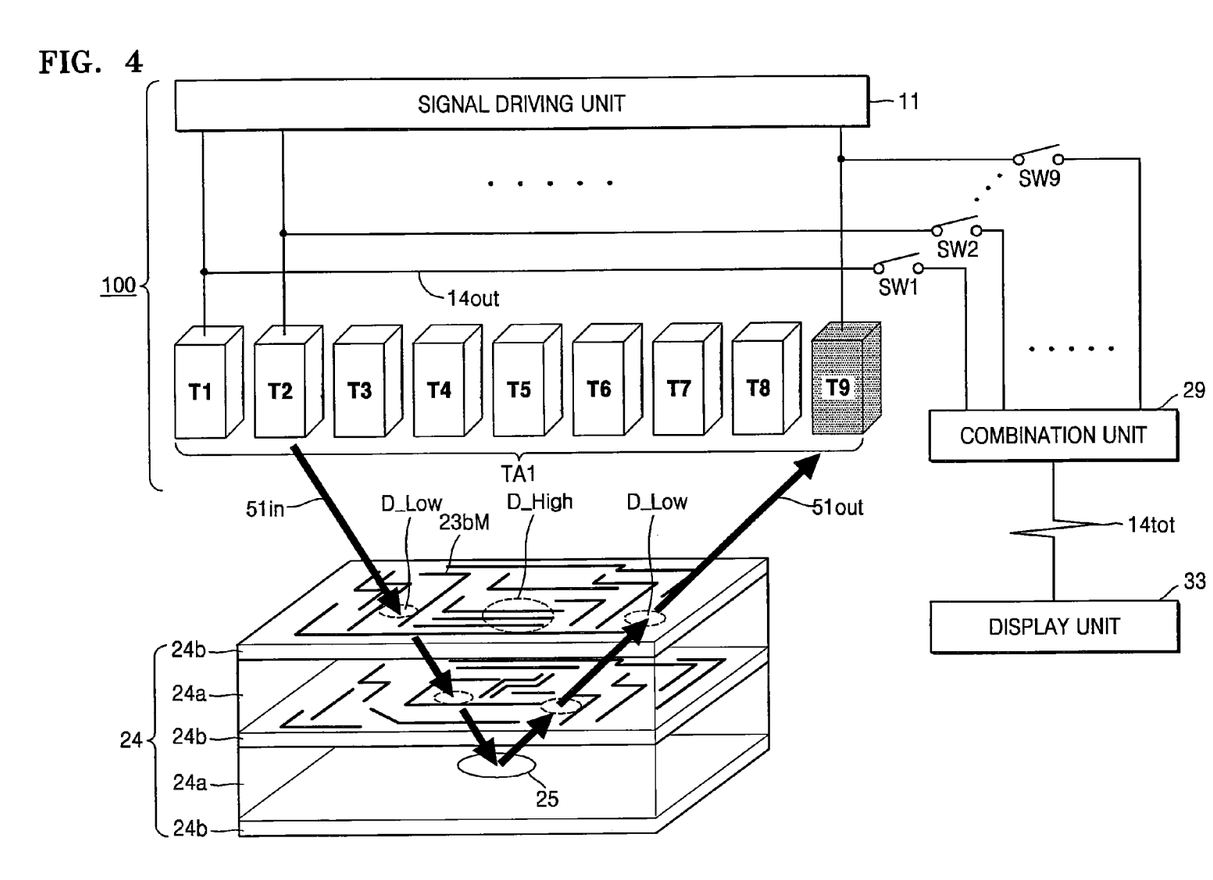
FIG. 4 is a diagram of an operation of a case where the test device of FIGS. 1 and 2 is used for testing another test target point.

FIG. 4 is a diagram of an operation of a case where the test device 100 of FIGS. 1 and 2 is applied for another test object.

Referring to FIG. 4, as described above with reference to FIGS. 1 to 2, the test device 100 may include a signal driving unit 11 that generates pulse signals (not illustrated), a time delay unit (not illustrated) that adjusts timings of the pulse signals, a plurality of transceivers T1 to T9 that receive timing-adjusted pulse signals 17in, transceive waves 51in and 51out to/from a test object 23, and output a plurality of received signals 17out, a combination unit 29 that combines a plurality of received signals 14out, and a plurality of switches SW1 to SW9 that select some of the received signals 14out transferred from the combination unit 29. The plurality of transceivers T1 to T9 may be arranged in a row to form a transceiver array TA1.

The test object 24 may be a semiconductor structure in which insulating layers 24a and metal wiring layers 24b are alternately stacked. As compared to the metal wiring layers 24b, the insulating layers 24a do not greatly influence the transmission of the waves 51in and 51out. However, since a plurality of metal wirings 24bM included in the metal wiring layers 24b hardly transmit the waves 51in and 51out, the reception sensitivities of the transceivers T1 to T9 may be rapidly reduced. The plurality of metal wirings 24bM may be irregularly arranged within the metal wiring layers 24b, with insulating materials being disposed therebetween. Therefore, even the same metal wiring layer 23b may have a region D_High with a high wiring density and a region D_Low with a low wiring density.

The plurality of transceivers T1 to T9 may generate a plurality of input waves (not illustrated) focused on the test target point 25 of the test object 24. However, the input wave 51in, which is generated by the second transceiver T2 and passes through the region D_Low with the low wiring density, may be the most valid input wave 51in that forms a plurality of reflected waves (not illustrated) received by the plurality of transceivers T1 to T9.

The plurality of reflected waves may be the same as the plurality of input waves. The plurality of transceivers T1 to T9 may receive reflected waves (not illustrated), respectively. However, the reflected wave 51out, which passes through the region D_Low with the low wiring density and is received by the ninth transceiver T9, may be the most valid reflected wave 51out having high reception sensitivity.

Except for the ninth switch SW9 receiving the received signal 14out transferred from the ninth transceiver T9, the first to eighth switches SW1 to SW8 connected to the first to eighth transceivers T1 to T8 may be opened. Therefore, it is possible to obtain the combined received signal 14tot having an increased reception sensitivity or the highest reception sensitivity with respect to the test target point 25.

For clarity and ease of representation, only the path of the input wave 51in transmitted from the second transceiver T2 and the path of the reflected wave 51 out received by the ninth transceiver T9 are illustrated in FIG. 4. However, in practice, there may exist any number of input waves and reflected waves that are transceived between the plurality of transceivers T1 to T9 and the test object 24. In addition, only one reflected wave 51out passing through the region D_Low with the low wiring density is illustrated, but there may exist two or more reflected waves.

In some exemplary embodiments, the plurality of switches SW1 to SW9 connected to the plurality of transceivers T1 to T9 may be selectively opened or closed in consideration of the wiring density of the metal wiring layer 24b existing on the reflected wave 51out and the disturbed reflected wave formed at the interface between the insulating layer 24a and the metal wiring layer 24b.

Figure 5:
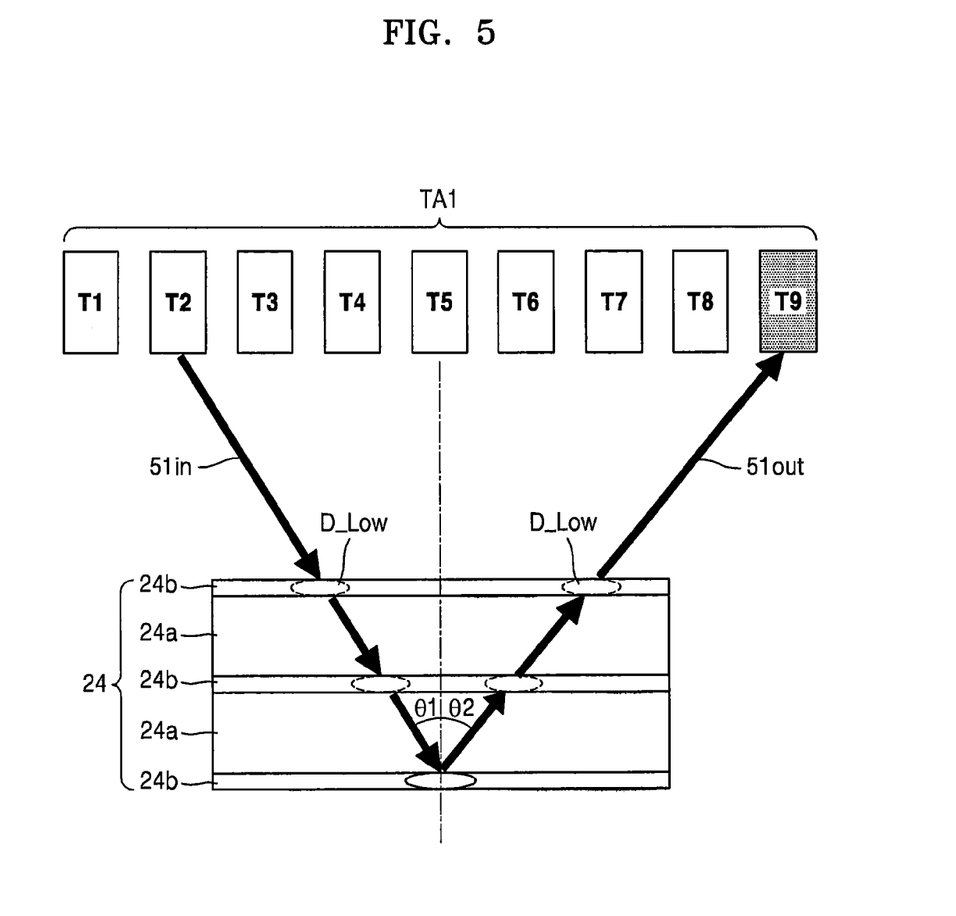
FIG. 5 is a diagram illustrating an input angle and a reflection angle of a wave input to the test device of FIG. 4.

FIG. 5 is a diagram illustrating an input angle and a reflection angle of a wave input on the test device 100 of FIG. 4.

Specifically, FIG. 5 illustrates the path of the most valid input wave 51in between the second transceiver T2 and the test target point 25 and the path of the most valid reflected wave 51 out between the test target point 25 and the ninth transceiver T9. An input angle θ1 formed between the input wave 51in and the normal line of the test target point 25 may not be equal to a reflection angle θ2 formed between the reflected wave 51out and the normal line of the test target point 25. As described above with reference to FIG. 4, since the wiring densities within the metal wiring layers are asymmetrical, the input angle θ1 of the most valid input wave 51in may not be matched with the reflected angle θ2 of the reflected wave 51out having the highest reception sensitivity.

Figure 6:
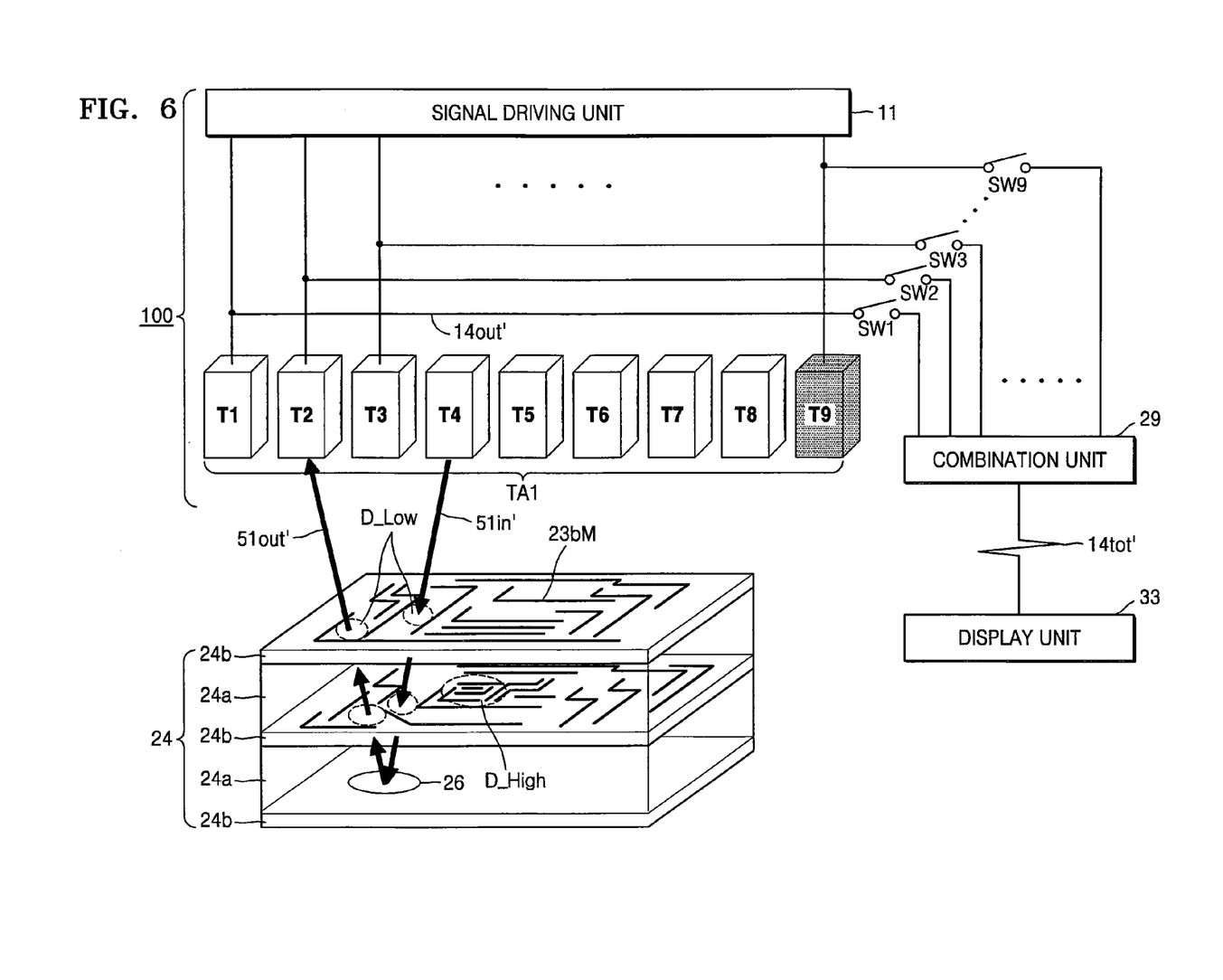
FIG. 6 is a diagram of an operation when the test device of FIG. 4 is used for testing a changed test target point.

FIG. 6 is a diagram of an operation of a case where the test device 100 of FIG. 4 is used for testing a changed test target point. For convenience of description, in FIG. 6, the test target point 25 of FIG. 4 is referred to as a first test target point 25.

Specifically, FIG. 6 illustrates the path of the most valid input wave 51in' when testing a second test target point 26 that is different from the first test target point 25 of FIG. 4 with respect to the same test object 24 and the path of the reflected wave 51out' having the highest reception sensitivity. Among a plurality of input waves (not illustrated), which are generated by the plurality of transceivers T1 to T9 and are input to the second test target point 26, the path of the input wave 51in' generated by the fourth transceiver T4 may pass through the region with the low wiring density and thus the corresponding wave may become the most valid input wave 51in'. Among a plurality of reflected waves (not illustrated), which are reflected from the second test target point 26 and are received by the plurality of transceivers T1 to T9, the path of the reflected wave 51out' received by the second transceiver T2 may pass through the region with the low wiring density and thus the corresponding wave may become the reflected wave 51out' having the highest reception sensitivity.

Except for the second switch SW2 receiving the received signal 14out' transferred from the second transceiver T2, the first switch SW1 and the third to eighth switches SW3 to SW8 connected to the first transceiver T1 and the third to eighth transceivers T3 to T8 may be opened. Therefore, it is possible to obtain the combined received signal 14tot' having the highest reception sensitivity with respect to the second test target point 26.

For clarity and ease of representation, only the path of the input wave 51in' transmitted from the fourth transceiver T4 and the path of the reflected wave 51out' received by the second transceiver T2 are illustrated in FIG. 6. However, in practice, there may exist input waves and reflected waves that are transceived between the plurality of transceivers T1 to T9 and the test object 24.

As described above, according to the exemplary embodiment, the test device 100 including the plurality of transceivers T1 to T9 may efficiently test all points of the test object 24, without being moved.

Figure 7:
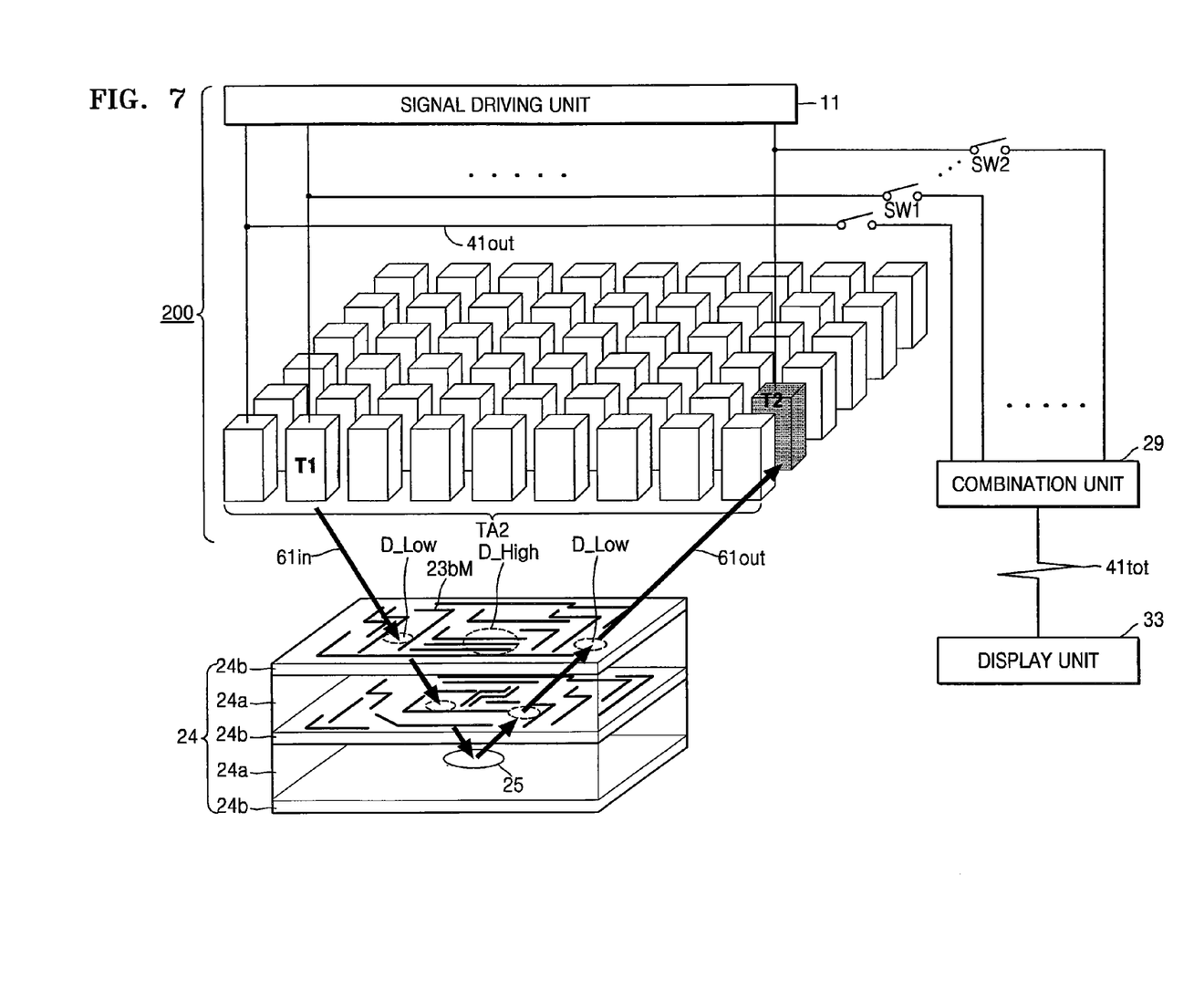
FIGS. 7 to 9 are diagrams illustrating test devices, according to exemplary embodiments of the inventive concept.
Figure 8:
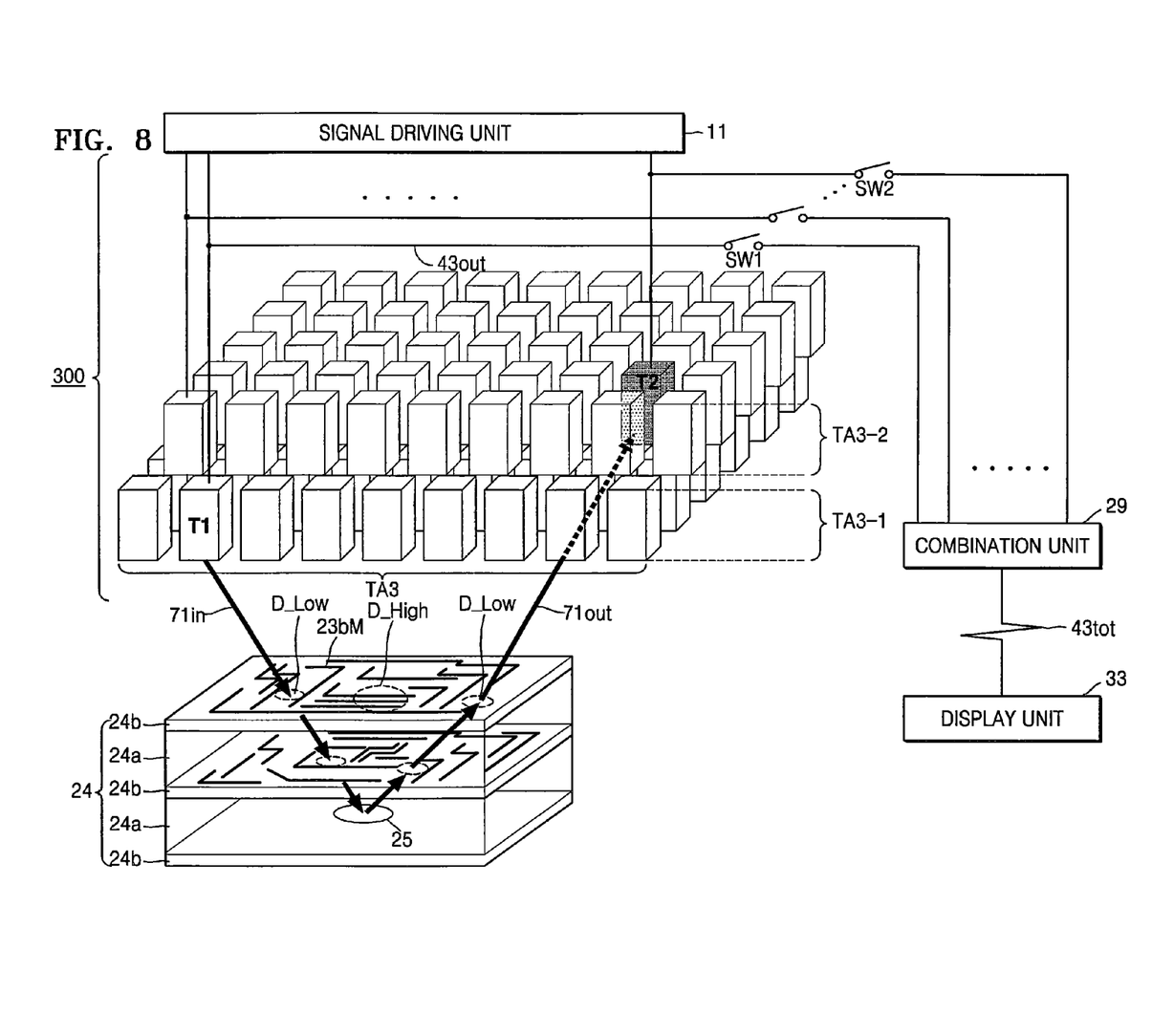
Figure 9:
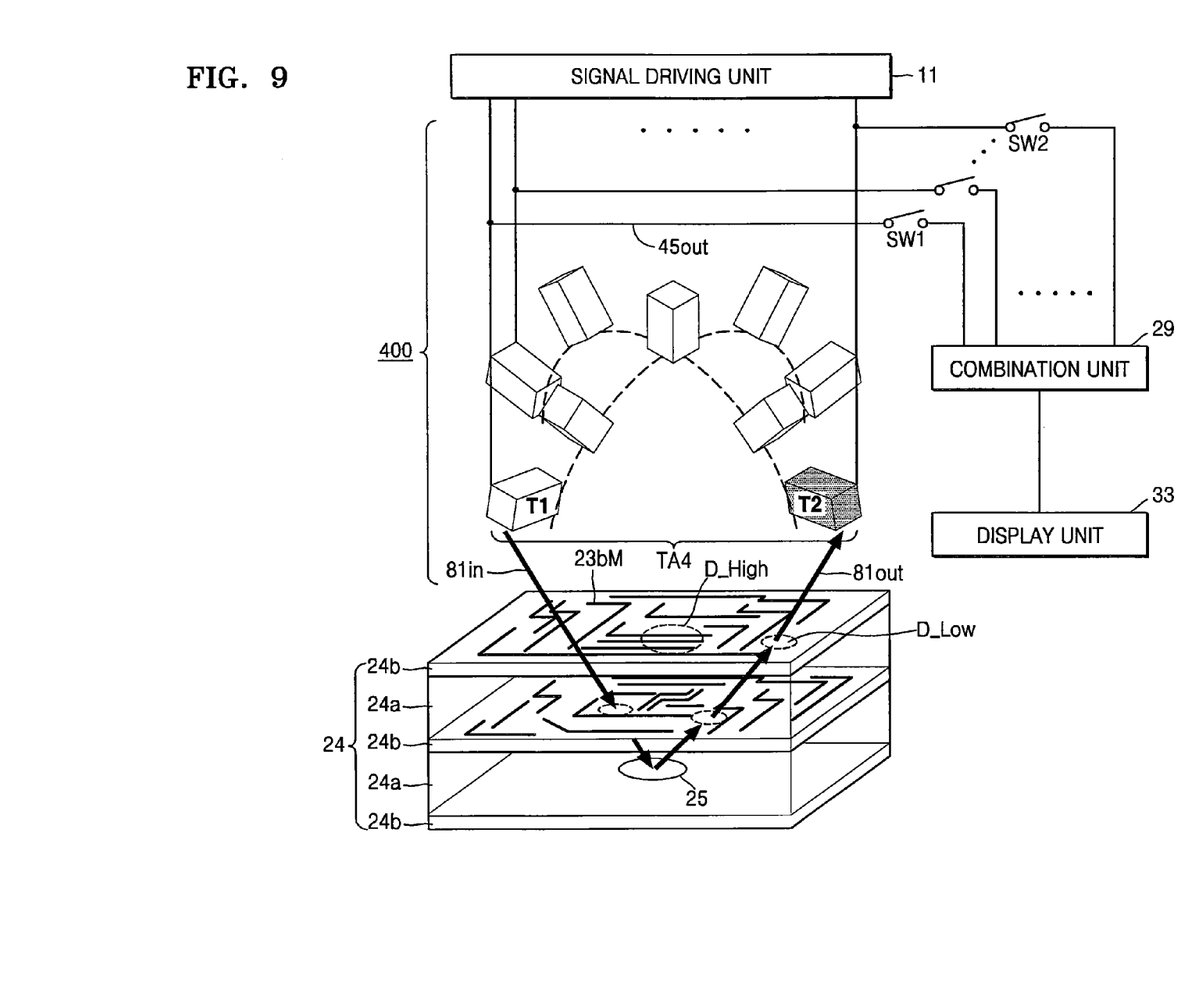

FIGS. 7 to 9 are diagrams illustrating test devices 200, 300, and 400, respectively, according to exemplary embodiments of the inventive concept. The test devices 200, 300, and 400 differ from the test device 100 described above with reference to FIGS. 1 to 6 in terms of the number of transceivers included therein. Reference symbols T1 to T9 used in FIGS. 7 to 10 are only used to distinguish a plurality of transceivers from one another, and do not refer to the same members.

Referring to FIG. 7, a plurality of transceivers included in the test device 200 may be arranged in a matrix form. For example, the test device 200 may have a transceiver array TA2 of a 9×6 matrix form. Since the plurality of transceivers are densely arranged, a plurality of input waves (not illustrated) and a plurality of reflected waves (not illustrated) passing through a region D_Low with a low wiring density may be increased. As a result, the reception sensitivities of the received signals may be increased.

In FIG. 7, an input wave 61in, which is generated by the first transceiver T1 of the first row in the transceiver array TA2, may be most valid, and a reflected wave 61out, which is received by the second transceiver T2 of the second row in the transceiver array TA2, may have the highest reception sensitivity. In the transceiver array TA1 of FIG. 4 in which the nine transceivers T1 to T9 are arranged in a row, it is analyzed that the reflected wave, which is received by the ninth transceiver T9 disposed at the end of the same row with respect to the same test target point 25 as that of FIG. 7, has the highest reception sensitivity. However, in the transceiver array TA2 included in the test device 200 of FIG. 7, the plurality of transceivers are arranged two-dimensionally more densely, and the combined received signal 41tot having higher reception sensitivity may be obtained at the second transceiver T2 disposed at the end of the second row.

Switches, which are connected to the transceivers other than the second transceiver T2 in the transceiver array TA2, may be opened. Therefore, it is possible to obtain the combined received signal 41tot having the highest reception sensitivity with respect to the test target point 25.

Referring to FIG. 8, a plurality of transceivers included in the test device 300 may be arranged to have a stack structure of matrix forms. For example, the test device 300 may include a double-layer transceiver array TA3 in which a first transceiver array TA3-1 of a 9×6 matrix form is disposed on the ground floor and a second transceiver array TA3-2 of an 8×5 matrix form is disposed on the second floor. At this time, in order to secure the path of the reflected wave transferred from the test target point 25, the first transceiver array TA3-1 and the second transceiver array TA3-2 may be offset from one another. Since the plurality of transceivers are densely arranged, a plurality of input waves (not illustrated) and a plurality of reflected waves (not illustrated) passing through a region D_Low with a low wiring density may be increased. As a result, the reception sensitivities of the received signals may be increased.

In FIG. 8, the most valid input wave 71in may be generated from the first transceiver T1 disposed at the second position of the first row of the first transceiver array TA3-1 disposed on the ground floor in the double-layer transceiver array TA3. A reflected wave 71 out, which is received by the second transceiver T2 disposed at the seventh position of the second row of the second transceiver array TA3-2 disposed on the second floor in the double-layer transceiver array TA3, may have the highest reception sensitivity.

Switches, which are connected to the transceivers other than the second transceiver T2 in the transceiver array TA2, may be opened. Therefore, it is possible to obtain the combined received signal 43tot having the highest reception sensitivity with respect to the test target point 25.

Referring to FIG. 9, a plurality of transceivers included in a test device 400 may be arranged in a spherical shape. For example, the test device 400 may have a transceiver array TA4 including a transceiver disposed at a first level highest from a test object 24, four transceivers disposed around at a second level lower than the first level, and four transceivers disposed at a third level lower than the second level. Since the plurality of transceivers are arranged at various positions and various angles, a plurality of input waves (not illustrated) and a plurality of reflected waves (not illustrated) passing through a region D_Low with a low wiring density may be increased. As a result, the reception sensitivities of the received signals may be increased.

In FIG. 9, the most valid input wave 81in may be generated from the first transceiver T1 disposed at the third level in the transceiver array TA4. A reflected wave 81out, which is received by the second transceiver T2 disposed at the third level in the transceiver array TA4, may have the highest reception sensitivity. Switches, which are connected to the transceivers other than the second transceiver T2 in the transceiver array TA4, may be opened. Therefore, it is possible to obtain the combined received signal 45tot having the highest reception sensitivity with respect to the test target point 25.

While the inventive concept has been particularly shown and described with reference to exemplary embodiments thereof, it will be understood that various changes in form and details may be made therein without departing from the spirit and scope of the following claims.

What is claimed is:

1. A test device comprising:
a plurality of transceivers configured to respectively transmit a wave to a test target point of a test object, to respectively receive a wave reflected, scattered, and/or refracted from the test object, and to respectively generate and output a signal in response to the received wave;
a combiner configured to combine the signals generated by the plurality of transceivers;
a plurality of switches configured to selectively transfer some of the signals to the combiner and to selectively block the others of the signals from being transferred to the combiner;
a switch control unit configured to control closing and opening of the plurality of switches to selectively transfer some of the signals to the combiner and to selectively block the others of the signals from being transferred to the combiner; and
wherein the test object comprises a semiconductor structure having an irregular wiring density comprising a first region having a first wiring density and a second region having a second wiring density, wherein the first wiring density is lower than the second wiring density,
wherein the switch control unit controls the plurality of switches such that at least one of the signals corresponding to the reflected, scattered, and/or refracted wave passing through the first wiring density is transferred to the combiner and others of the signals are blocked.

2. The test device of claim 1, wherein the waves transmitted by the plurality of transceivers are focused on the test target point.

3. The test device of claim 1, wherein the wave received by any one of the plurality of transceivers includes waves reflected, scattered, and/or reflected in response to the waves transmitted by the other transceivers.

4. The test device of claim 1, wherein the switch control unit closes the switch corresponding to at least one of the signals having a reduced level of noise from among the generated signals and opens the switches corresponding to the other generated signals.

5. The test device of claim 1, wherein the plurality of switches are further configured so that opening and closing thereof are reset according to a change of the test target point.

6. The test device of claim 1, wherein an input angle of the wave transmitted from any one of the plurality of transceivers to the test target point is different from a reflection angle of the wave received by the transceiver in a predefined plane, which corresponds to the received signal transferred to the combiner.

7. The test device of claim 1, wherein the plurality of transceivers are arranged in a matrix form.

8. The test device of claim 1, wherein the plurality of transceivers are arranged in a multilayer structure.

9. The test device of claim 1, wherein the plurality of transceivers are arranged in a spherical shape.

10. The test device of claim 1, wherein the wave is a sound wave, and each of the transceivers comprises a piezoelectric element that receives the reflected, scattered, or refracted wave from the test object and converts the received wave into an electric signal.

11. The test device of claim 1, wherein the wave is an electromagnetic wave, and each of the transceivers comprises a photoelectric element that receives the reflected, scattered, or refracted wave from the test object and converts the received wave into an electric signal.

12. The test device of claim 1, further comprising a display unit configured to display an image of the test object in response to the generated signals transferred to the combiner.

13. An ultrasonic imaging device comprising:
a plurality of ultrasonic transceivers, each of the plurality of ultrasonic transceivers including a piezoelectric element that is configured to transmit an ultrasonic wave to a test object and is configured to receive an echo ultrasonic wave generated from the test object and generate and output a signal in response to the received echo ultrasonic wave;
a combiner that combines the signals generated by the plurality of ultrasonic transceivers; and
a plurality of switches between the plurality of ultrasonic transceivers and the combiner, the plurality of switches being configured to open or close to selectively transfer the generated signals to the combiner or to selectively block the generated signals from being transferred to the combiner,
wherein the plurality of switches are further configured to close and selectively block at least one of the signals that contains a relatively high level of noise from among the generated signals and the opening and closing of the plurality of switches are reset according to a change in a position of the test object; and
a switch control unit configured to control closing and opening of the plurality of switches to selectively transfer some of the signals to the combiner and to selectively block others of the signals from being transferred to the combiner;
wherein the test object comprises a semiconductor structure having an irregular wiring density comprising a first region having a first wiring density and a second region having a second wiring density, wherein the first wiring density is lower than the second wiring density, and
wherein the switch control unit controls the plurality of switches such that at least one of the signals corresponding to reflected, scattered, or refracted wave passing through the first wiring density is transferred to the combiner and others of the generated signals are blocked.

* * * * *